United States Patent [19]
Epstein et al.

[11] Patent Number: 5,782,860
[45] Date of Patent: Jul. 21, 1998

[54] CLOSURE DEVICE FOR PERCUTANEOUS OCCLUSION OF PUNCTURE SITES AND TRACTS IN THE HUMAN BODY AND METHOD

[75] Inventors: Gordon H. Epstein, Fremont; Todd E. Lempert, Piedmont, both of Calif.

[73] Assignee: BioInterventional Corporation, Pleasanton, Calif.

[21] Appl. No.: 798,870

[22] Filed: Feb. 11, 1997

[51] Int. Cl.$^6$ ............................................. A61B 17/04
[52] U.S. Cl. ............................................. 606/213
[58] Field of Search ..................... 606/213; 604/15, 604/285–288

[56] References Cited

U.S. PATENT DOCUMENTS

| | | | |
|---|---|---|---|
| 4,744,364 | 5/1988 | Kensey | 128/334 |
| 4,852,568 | 8/1989 | Kensey | 128/325 |
| 4,890,612 | 1/1990 | Kensey | 606/213 |
| 5,171,259 | 12/1992 | Inoue | 606/213 |
| 5,383,896 | 1/1995 | Gershony et al. | 606/213 |
| 5,454,833 | 10/1995 | Boussignac et al. | 606/213 |

OTHER PUBLICATIONS

Datascope Corporation, "VasoSeal" product brochure, 1991.
Sherwood, Davies & Geck, "AngioSeal" product brochure, 1977.

*Primary Examiner*—Gary Jackson
*Attorney, Agent, or Firm*—Flehr Hohbach Test Albritton & Herbert LLP

[57] ABSTRACT

A closure device for percutaneously forming a closure of a puncture in the tissue of human body. The device comprises a flexible elongate tubular member having proximal and distal extremities and a longitudinal axis. The flexible elongate tubular member has a first lumen extending from the proximal extremity to the distal extremity. A closure assembly is carried by the distal extremity of the flexible elongate tubular member and is movable between contracted and expanded positions. The closure assembly includes a closure mechanism covered by an impermeable membrane. A handle is carried by the proximal extremity of the flexible elongate tubular member and is adapted to be grasped by the human hand. A deployment mechanism is carried by the handle and extends through the flexible elongate tubular member and is coupled to the closure assembly for moving the closure assembly from the contracted position to the expanded position.

42 Claims, 5 Drawing Sheets

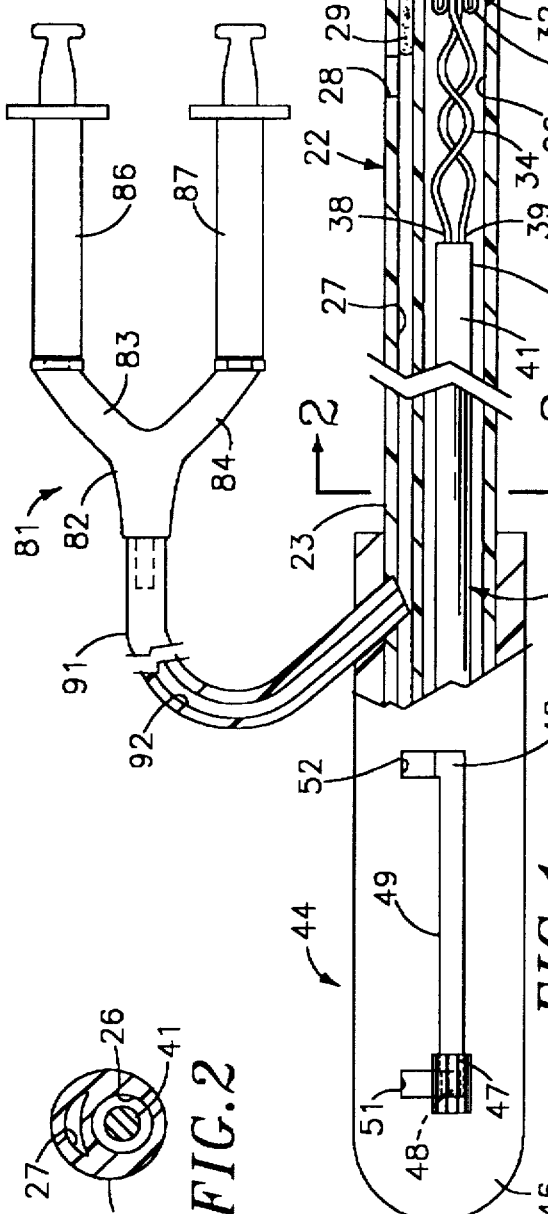
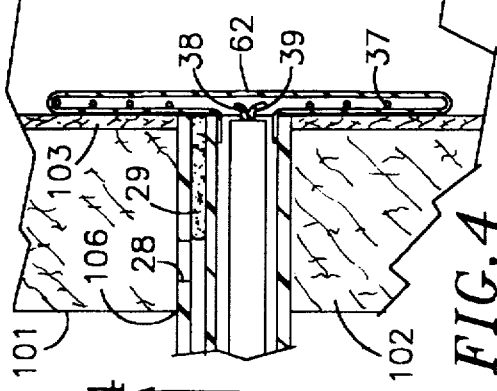
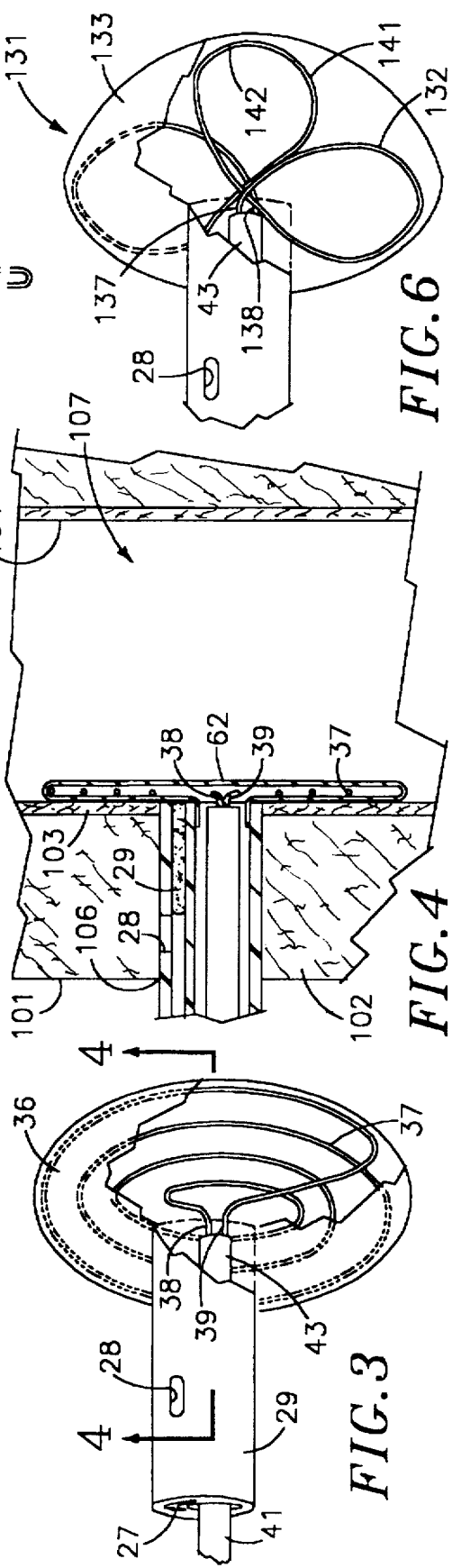
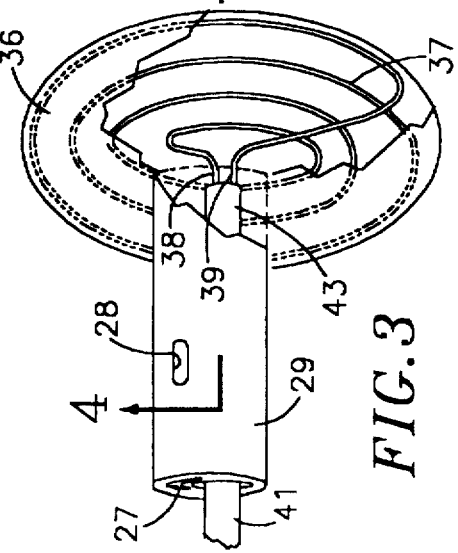
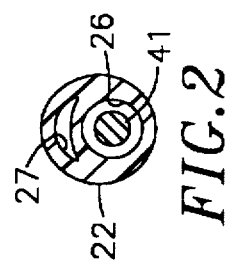

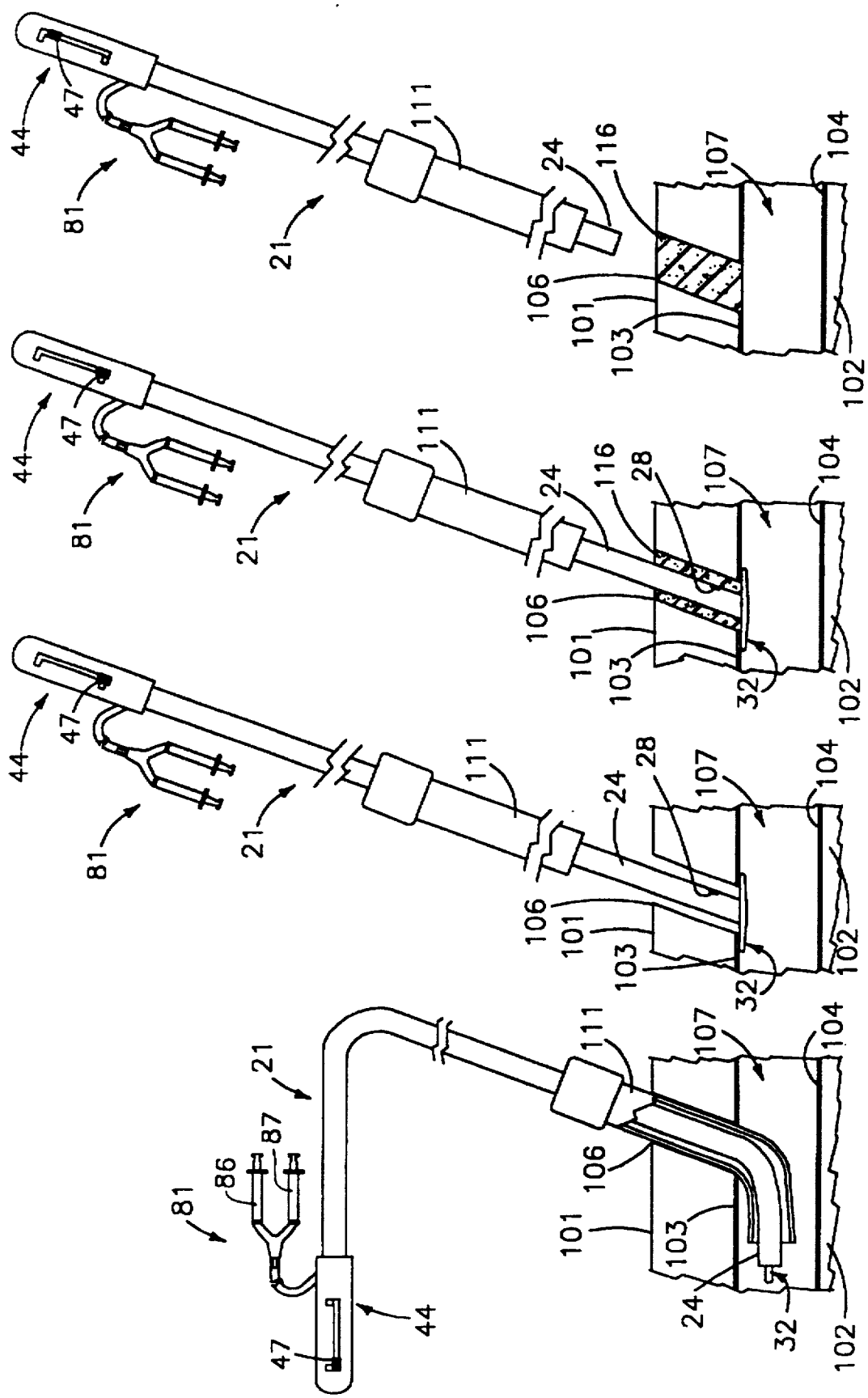

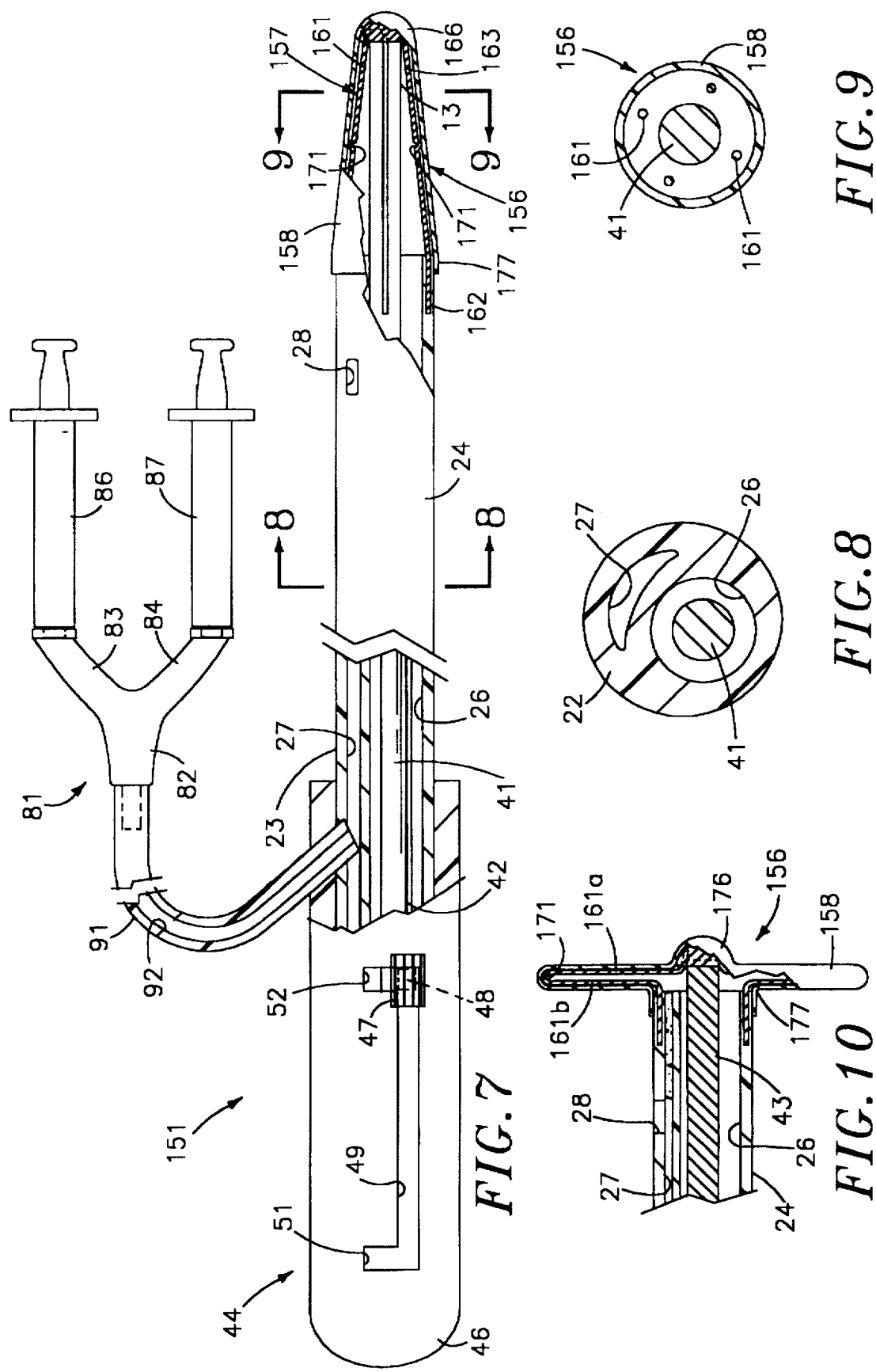

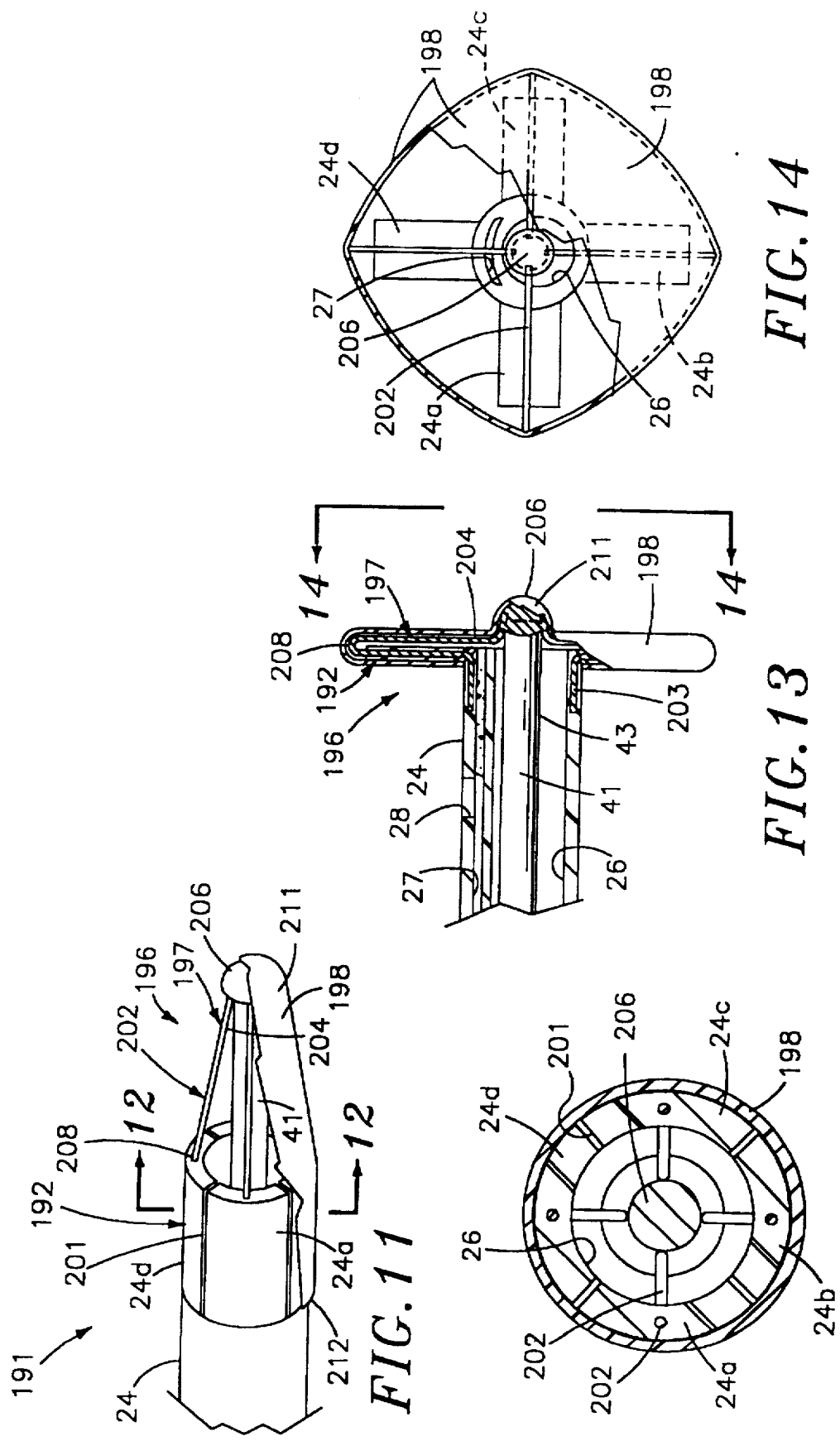

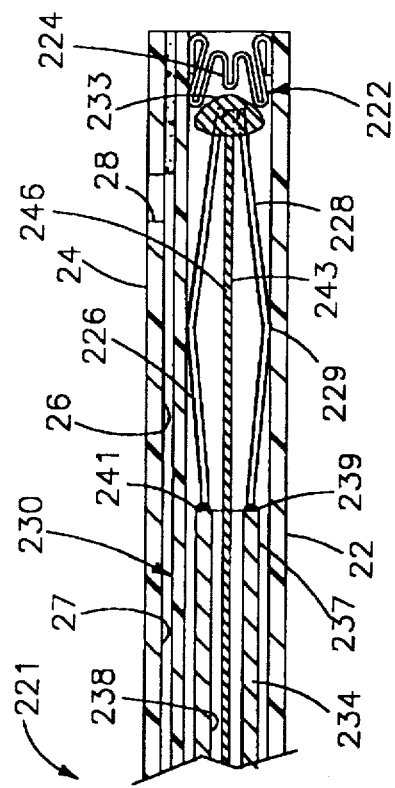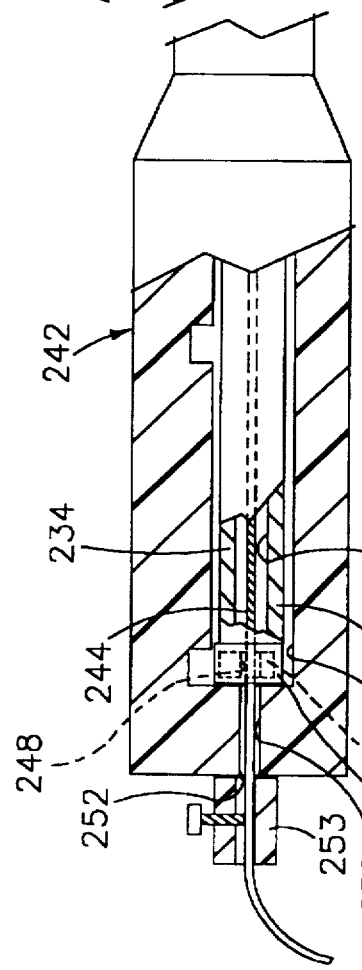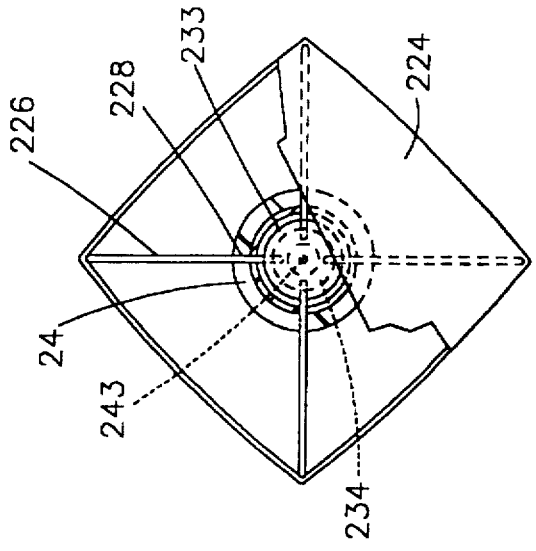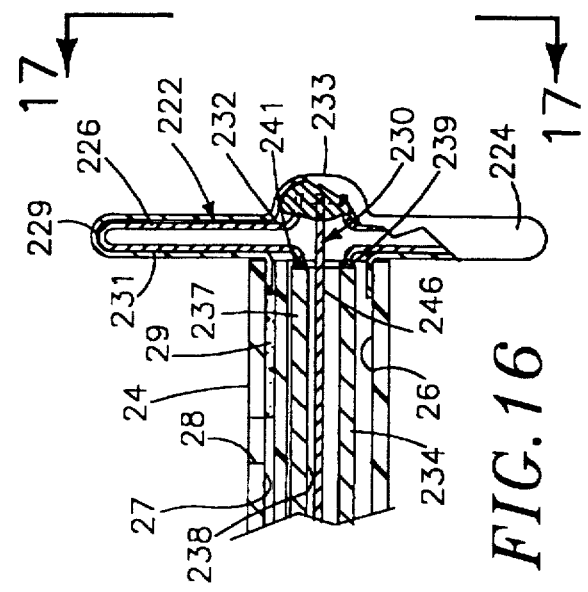

CLOSURE DEVICE FOR PERCUTANEOUS OCCLUSION OF PUNCTURE SITES AND TRACTS IN THE HUMAN BODY AND METHOD

This invention relates to a closure device and method for percutaneous access and occlusion of puncture sites, natural tracts and more particularly to vascular access sites in the human body.

Percutaneous access to the blood vessels and organs of the human body for diagnosis and treatment of disease processes has heretofore been accomplished. Percutaneous vascular procedures are performed involving the coronary, peripheral and cerebral vasculature. These procedures include coronary and peripheral angiography, angioplasty, atherectomies, coronary retroperfusion and retroinfusion, cerebral angiograms, treatment of strokes, cerebral aneurysms and the like. Patients undergoing such procedures are often treated with anti-platelet drugs, anticoagulants such as heparin, thrombolytics, or a combination thereof, all of which interfere with coagulation making it more difficult for the body to seal a puncture site. Various devices and methods have heretofore been utilized, however, they all have had deficiencies, including the use of complicated devices and methods. In addition, difficulties are still encountered in obtaining good seals. There is therefore a need for a device and method for percutaneous access and occlusion of vascular access sites and other puncture sites and natural tracts in the human body which overcome the deficiencies of prior art devices and methods.

In general, it is an object of the present invention to provide a closure device and method for percutaneous access and occlusion of vascular access sites, other puncture sites and natural tracts in the human body which will make possible a positive seal of the puncture site or tract promoting rapid healing of the puncture site or tract.

Another object of the invention is to provide a closure device and method of the above character which can be easily and reliably used.

Another object of the invention is to provide a closure device and method of the above character in conjunction with which a biological sealant is used by introduction into the puncture site or natural tract.

Another object of the invention is to provide a closure device and method of the above character which leaves a small enough opening after removal of the closure device so that the biological sealant will seal the remaining opening.

Another object of the invention is to provide a closure device and method of the above character which enables continued substantially unobstructed blood flow during deployment and use of the closure device.

Another object of the invention is to provide a closure device and method of the above character in which no foreign body remains in the blood vessel.

Another object of the invention is to provide a closure device and method of the above character that permits early ambulation of patients and avoids prolonged bed rest.

Another object of the invention is to provide a closure device and method of the above character which reduces the risk of bleeding, formation of arteriovenous fistula, formation of pseudoaneurysm, thrombosis with distal embolization and infection.

Another object of the invention is to provide a closure device and method of the above character that reduces the risk of causing ischemia of an extremity.

Another object of the invention is to provide a closure device and method of the above character that is inexpensive, quick, safe, easy to use and is disposable.

Additional objects and features of the invention will appear from the following description in which the preferred embodiments and the methods using the same are described in conjunction with the accompanying drawings.

FIG. 1 is a side-elevational view partially in section of a closure device for obtaining percutaneous access and occlusion of puncture sites in the human body incorporating the present invention and having closure means in a de-deployed or retracted position.

FIG. 2 is a cross-sectional view taken along the line 2—2 of FIG. 1.

FIG. 3 is a side-elevational isometric view of the distal end of the device shown in FIG. 1 with the closure means in a deployed or extended position.

FIG. 4 is a cross-sectional view taken along the line 4—4 of FIG. 3 and shows the manner in which a seal is formed with respect to a puncture.

FIGS. 5A–5D are cartoons demonstrating the method of using the device of the present invention for occluding a vascular access or puncture site.

FIG. 6 is a partial isometric view of an alternative closure assembly for the closure device shown in FIG. 1.

FIG. 7 is a side-elevational view partially in section of another embodiment of the closure device incorporating the present invention.

FIG. 8 is a cross-sectional view taken along the line 8—8 of FIG. 7.

FIG. 9 is a cross-sectional view taken along the line 9—9 of FIG. 8.

FIG. 10 is a side-elevational isometric view of the distal end of the device of FIG. 8 with the closure assembly in a deployed or expanded position.

FIG. 11 is a side-elevational view partially in section of another embodiment of the closure device incorporating the present invention.

FIG. 12 is a cross-sectional view taken along the line 12—12 of FIG. 11.

FIG. 13 is a partial side-elevational view of the distal extremity of the closure device of FIG. 11 with the closure mechanism in a deployed position.

FIG. 14 is a view looking along the line 14—14 of FIG. 13.

FIG. 15A is a side-elevational view partially in section of the proximal end of another embodiment of the closure device incorporating the present invention.

FIG. 15B is a side-elevational view partially in section of the distal end of the embodiment shown in FIG. 15A.

FIG. 16 is a side-elevational view partially in section of the distal end of the device of FIG. 15 with the closure assembly in a deployed position.

FIG. 17 is a view partially in section taken along the line 17—17 of FIG. 16.

In general, the closure device of the present invention is used for the percutaneous occlusion of a puncture site and natural tract in the human body. The human body has an outer layer of skin and inner layers of tissue surrounding a blood vessel having a lumen therein defined by a vessel wall. A puncture site traverses these layers and, in the case of a vascular access puncture, the vessel wall. The closure device comprises a flexible elongate tubular member having a longitudinal axis and having proximal and distal extremities. The flexible elongate tubular member has a first lumen extending therethrough from the proximal extremity to the distal extremity. A closure assembly is carried by the distal extremity and includes a closure mechanism and an impermeable membrane at least partially covering the closure mechanism. A handle is carried by the proximal extremity of the flexible elongate tubular member and is adapted to be grasped by the human hand and includes deployment means extending through the flexible elongate tubular member and coupled to the closure assembly for moving the closure assembly from a de-deployed or contracted position for introduction into and through a puncture to a deployed position for forming a seal occluding the puncture.

More specifically, as shown in FIGS. 1–4, the closure device 21 of the present invention for percutaneous occlusion of puncture sites and natural tracts consists of a flexible elongate tubular member 22 formed of a suitable plastic material such as polyethylene or polyurethane. The flexible elongate tubular member 22 has a longitudinal axis and proximal and distal extremities 23 and 24. The flexible elongate tubular member 22 is provided with a main circular in cross-section first lumen 26 which may be centrally disposed extending from the proximal extremity 23 to the distal extremity 24. It is also provided with an additional or second lumen 27 which may be crescent-shaped as shown in cross-section in FIG. 2 extending from the proximal extremity 23 to the distal extremity 24 where it opens through an external port 28. A plug 29 of a suitable material such as plastic is placed in the lumen 27 to occlude the lumen 27 distal of the port 28.

The flexible elongate tubular member 22 is of a suitable size, as for example a diameter ranging from 1–6 French corresponding to an outside diameter ranging from approximately 0.3 to 2.0 millimeters. The flexible elongate tubular member has a suitable length as for example 15–30 centimeters with the external port 28 being disposed a suitable distance adjacent to and proximal of the closure assembly 32, as for example from 2–4 millimeters up to several centimeters. The first lumen 26 may have an inside diameter of approximately 0.020" (0.5 mm) while the second lumen 27, if crescent-shaped may have a long axis dimension of approximately 0.030" to 0.040" (0.76 to 1 mm).

Closure means in the form of a closure or expansion assembly 32 is carried by the distal extremity 24 of the flexible elongate tubular member 22 and is coupled or secured to deployment means or mechanism 33 for movement from a contracted, retracted or de-deployed position to an expanded or deployed position. The closure assembly 32 includes a closure mechanism that is an expansile or working member 34 and an impervious membrane 36 which covers the closure mechanism 34. The closure mechanism 34 as shown in FIGS. 3 and 4 is in the form of a complex geometrical configuration, as for example a coil, when in a free state. The coil 34 is formed of a suitable material which can be elongated without permanent deformation but when freed or unconstrained has a substantial portion thereof which will return to a generally planar or disk-like configuration to which it has been annealed. One material found to be particularly suitable for such an application is a superelastic or shape memory element as formed of a nickel/titanium alloy, often called Nitinol. The coil 34 has a plurality of generally circular turns 37 and has first and second ends 38 and 39 secured to the deployment mechanism 33 in a manner hereinafter described. The turns 37 of the coil 34 lie in a single plane which is generally perpendicular to the longitudinal axis of the flexible elongate tubular member 22.

The coil 34 has a diameter which is selected to overlap a puncture site as hereinafter described to occlude the puncture site. Typically, a suitable diameter such as 3 to 7 millimeters and preferably approximately 5 millimeters is used. In the de-deployed configuration the constrained coil 34 has a suitable diameter ranging from 1 mm to 2.0 mm.

The coil 34 can be formed of wire having a diameter ranging from 0.002" to 0.004" (0.05 to 0.1 millimeters) and preferably about 0.003" (0.076 millimeters). Alternatively, it can be formed of ribbon generally rectangular in cross-section and can have a thickness of approximately 0.001" to 0.002" (0.025 to 0.05 mm.) and a width of approximately 0.003" to 0.005" (0.076 to 0.13 millimeters).

The deployment means or mechanism 33 consists of a push-pull wire 41 which is slidably disposed in and extending through the first or main lumen 26 and has proximal and distal extremities 42 and 43. The push-pull wire 41 is formed of a suitable material such as stainless steel and has a suitable diameter as for example 0.008" to 0.032". Means is provided for securing the two ends 38 and 39 of the coil 34 to the distal extremity 43 of the push-pull wire 41 and consists of solder forming joints. As shown in FIG. 1 the proximal end 42 of the push-pull wire 41 extends out of the proximal extremity 23 of the flexible elongate tubular member 22 and is operatively connected to a handle assembly 44 as hereinafter described.

The handle assembly 44 is formed of a body 46 of suitable material such as plastic and is mounted on the proximal extremity 23 of the flexible elongate tubular member 22. The handle 44 is sized so it is adapted to be grasped by the human hand and is provided with means for operation of the push-pull wire 41 which includes a button 47 adapted to be engaged by a finger of the hand holding the handle. The button 47 is mounted on a protrusion 48 which is slidably mounted in a longitudinally extending slot 49 in the handle 44 and is movable between first and second positions for deploying the coil 34 from a retracted or contracted elongate position constrained within the flexible elongate tubular member 22 to an expanded position outside of the tubular member 22. The proximal extremity 42 of the push-pull wire 41 is secured to the protrusion 48 in a suitable manner such as a wire clamp or adhesive (not shown). The slot 49 opens into sideways extending notches 51 and 52 provided in the body which can receive the protrusion 48 in either the first or second position to retain the push-pull wire 41 in the desired position as hereinafter described.

The closure means 32 also includes a flexible impermeable membrane 36 which is carried by and secured to the distal extremity 24 of the flexible elongate tubular member 22. It is desired that this membrane 36 be very flexible and it therefore has a wall thickness ranging from 0.0005" to 0.003" (0.0127 to 0.076 millimeters) and preferably 0.001" (0.025 millimeters). It can be formed of any suitable flexible impermeable material such as elastomeric and non-elastomeric materials. For example, latex or silicone have been found to be suitable. The membrane 36 should be substantially impermeable to blood and other liquids. It is preferably formed as a tubular sock which can have an elongate generally cylindrical configuration with one closed end 54 and the other end circumscribed by an opening 56 which is defined by a rim 57 of the impermeable membrane. This rim 57 is circumferentially secured to the distal extremity 24 in a suitable manner such as by an adhesive (not shown) and preferably interiorly within the first or main lumen 26. However, if desired, the rim 57 can also be affixed exteriorly to the outer surface of the tip 31 of the distal extremity 24 of the flexible elongate tubular member 22. The impermeable membrane 36 is formed in such a manner so that it can, upon manufacture of the device 21, be disposed internally of the distal extremity 24 of the flexible elongate tubular member 22 and be folded inwardly with folds 58 in the main lumen 26 to accommodate closure mechanism 34 in a constrained, retracted or contracted or de-deployed position as shown in FIG. 1. It also has the flexibility of being moved outwardly by operation of the push-pull wire 41 to the sock-like dotted line position 61 shown in FIG. 1.

The impermeable membrane 36 also can be caused to assume a disk-like planar configuration as shown by the dotted-line position 62 in FIG. 1. This is accomplished by operation of the deployment mechanism 33 to move the push-pull wire 41 distally to urge the closure mechanism 34 distally to move out of the lumen 26 into the dotted-line position 61. As soon as the closure mechanism 34 is clear of the main lumen 26, it will expand into its memorized configuration. As this expansion is occurring, the membrane 36 covering the coil 34 is caused to move from the sock-like configuration 61 to the disk-like circular configuration 62 so that the membrane 36 is disposed on opposite sides of the closure mechanism 34 and lies in generally parallel planes which are generally perpendicular to the longitudinal axis of the flexible elongate tubular member 22 for percutaneously occluding a puncture as hereinafter described. The deployed closure mechanism 34 is sufficiently rigid so as to provide a supporting framework for the membrane 36.

The closure device 21 also consists of biological sealant introducer means 81 carried by the handle 44 and the flexible elongate tubular member 22 for introducing a biological sealant into a puncture proximal of the closure assembly 32 after the closure assembly 32 has been positioned. The biological sealant is of a suitable type such as a two-component fibrin glue, collagen, Avitene (trademark), Gelfoam (trademark), cellulose, gelatin, and mixtures or slurries thereof. It should be appreciated that other biological sealants or pharmacological agents may also be introduced into a puncture utilizing this device.

The biological sealant introducer means 81 can consist of a fitting of a suitable type such as a wye adapter 82 which is provided with first and second arms 83 and 84 with first and second syringes 86 and 87 removably mounted thereon on and containing the two separate constituents of fibrin glue being used as the biological sealant. The fitting 82 is connected to a flexible tubular member 91 which is sealed into the handle 44 and is provided with a lumen 92 therein in communication with the lumen (not shown) of the arms 83 and 84. The distal end of the flow passage 92 in the tubular member 91 is aligned to be in communication with the second lumen 27 of the flexible elongate tubular member 22 so that when the syringes 86 and 87 are operated the biological sealant components are mixed and pass through the flow passage 92 existing via the external port 28 of the second lumen 27.

Operation and use of the device 21 in performing the method of the present invention in the percutaneous access and occlusion of vascular access sites and other puncture sites in the human body may now be described in conjunction with the cartoons shown in FIGS. 5A–5D. Let it be assumed that a percutaneous femoral arterial catheterization is to be performed. After sterile preparation, a thin-walled hollow needle with syringe (not shown) is percutaneously inserted through the skin 101, the underlying subcutaneous tissue 102 and then through the wall 103 defining the lumen 104 of a vessel 107 such as the femoral artery to form a puncture 106. Intra-arterial access is confirmed by the aspiration of arterial blood. A flexible wire (not shown) is then passed through the needle into the artery 107 and the needle is removed, leaving only the wire in place in the puncture 106. A vessel dilator (not shown) with a shorter conventional over-lying sheath 111 is passed over the wire through the puncture 106 into the lumen 104 after which the wire and dilator are removed. The sheath 111 extends from outside the patient through skin 101 and subcutaneous tissues 102 and through the wall 103 into the lumen 104 as shown in FIG. 5A. Various diagnostic and therapeutic catheters and other similar medical devices can be passed through the sheath 111, whose diameter can range from 3 to 18 French, to perform desired procedures, as for example an angioplasty procedure during which time anti-coagulants such as heparin have been introduced. At the conclusion of any such procedure, such instruments are removed leaving only the sheath 111 in place.

Let it be assumed that it is now desired to seal the puncture 106. The closure device 21 of the present invention with the closure assembly 32 in the retracted position as shown in FIG. 1 is inserted into the sheath 111 while maintaining standard sterile precautions. The distal extremity 24 of the flexible elongate tubular member 22 is passed through the sheath 111 and into the lumen 104 so that it extends a short distance up to several inches beyond the distal extremity of the sheath 111 as shown in FIG. 5A. The sheath 111 is then slowly, incrementally withdrawn proximally while maintaining the device 21 as stationary as possible. As can be seen from FIG. 5B, the flexible elongate tubular member 22 has a length so that the sheath can be removed from the puncture 106 while retaining the distal extremity 24 in the lumen 104 and without removing the handle 44. When the sheath 111 has been withdrawn as shown in FIG. 5B, the closure assembly 32 may be deployed by operation of the deployment mechanism 33. Alternatively, the distal extremity 24 of the flexible elongate tubular member 22 can be passed into the lumen 104 a slightly greater distance, the device 21 deployed with the sheath 111 still in position, and then both the sheath 111 and device 21 slowly withdrawn so that the sheath 111 is removed from the lumen 104 with the deployed device 21 appropriately positioned in the lumen 104.

Before deployment of the closure assembly 32, the finger button 47 is in its most proximal-most position with the protrusion 48 being seated in the notch 51 as shown in FIG. 5A. Now let it be assumed that it is desired to move the closure assembly 32 from a contracted or retracted position where it is disposed within the first main lumen 26. When it is desired to move the closure assembly 32 to an expanded or open position, the button 47 is retracted from the notch 51 and slidably advanced along the slot 49 to push the distal extremity 43 of the push-pull wire 41 distally to cause the Nitinol closure mechanism 34 to be advanced distally and to carry the folded impermeable membrane 36 out of the first or main lumen 26 to cause it to assume a sock-like shape as shown in position 61 in FIG. 1. Continued forward movement of the finger button 47 causes further longitudinal movement of the push-pull wire 41 which causes further distal movement of the closure mechanism 33 until it clears the first lumen 26 so that it is substantially free to cause it to expand into its super-elastic or shape memory form of a coil to carry with it the flexible impervious membrane 36 to assume the disk-like configuration represented by position 62 as shown in FIGS. 1 and 4. The finger knob is then positioned so that the protrusion 48 is seated in the notch 52.

After the closure mechanism has been fully deployed, the handle 44 can be utilized to gradually retract the flexible elongate member 22 to ensure that the proximal surface of the flattened flexible membrane 36 is brought into close engagement with the inner surface of the wall 103 forming the lumen 104 in which the closure assembly 32 is disposed. This forms a liquid tight seal between the closure assembly 32 and the wall 103 immediately adjacent the puncture 106 which in turn enables accurate and effective deposition of the biological sealant into the puncture 106 as hereinafter described. Such a liquid tight seal is also necessary in connection with the present invention to prevent the leakage of blood through the puncture 106. This serves to prevent blood from interfering with attempts to safely and permanently occlude and seal the puncture 106 and to prevent inadvertent intravascular deposition of sealant.

The formation of a good seal between the occlusion assembly 32 and the wall 103 of the vessel 107 can be ascertained in several ways. By way of example the absence of arterial blood in the puncture 106 serves to verify that a good seal has been made. Attempts to aspirate blood from the second lumen 27 with no blood return therefrom also indicates accurate placement of the device 21. Alternatively, fluoroscopy can be utilized to check the position of the closure assembly 32. This is made possible because of the radio opacity of the closure mechanism 34. Radio opaque dyes may also be utilized to ascertain whether the puncture has been effectively sealed. A small amount of radio opaque dye may be injected into the subcutaneous tissue adjacent the puncture 106. If fluoroscopy demonstrates intravascular dye then there is inadequate placement of the closure assembly 32. If perchance there is any leakage, the button 47 can be engaged by the finger and retracted out of the notch 52 and proximally for a slight distance and then moved distally to re-deploy the mechanical assembly 32, thereafter grasping the handle 44 and pulling the flexible elongate member 22 proximally to again reestablish a seal with the wall 103 adjacent the puncture 106.

As soon as it has been established that a good seal has been formed in the manner hereinbefore described between the closure assembly 32 and the wall 103 adjacent the puncture 106, a biological sealant to be utilized can be introduced into the puncture 106 to provide a sealant 116 which extends throughout the puncture 106 from immediately outside the vessel 107 up to as far as the outer surface of the skin 101 as shown in FIG. 5C. It should be appreciated, however, that it may not be necessary to introduce an amount of sealant so great as to cause it to extend proximally to the skin. Assuming that the biological sealant is a fibrin glue supplied in two ports in the syringes 86 and 87, the physician utilizing the closure device 21 while holding the handle 44 in one hand utilizes the other hand to operate the syringes 86 and 87 to cause the constituents of the biological sealant to be introduced into the wye adapter 82 where they are mixed with each other and introduced through the tubular member 91 and into the second lumen 27, thence through the exit port 28 which is adjacent the closure assembly 32. It should be appreciated that in addition to holding the handle 44 in order to maintain engagement of the closure assembly 32 with the vessel wall 103, any suitable device by way of example a pin-vise may be applied to the flexible elongate tubular member 22 immediately adjacent the skin 101 so that the engagement is maintained and the physician has a free hand. The fibrin glue seals the innermost tissue layers in the puncture 106 and then, as hereinbefore described, can backfill the puncture 106 through the subcutaneous tissue 102 and to the skin 101, surrounding the distal extremity 24 of the flexible elongate tubular member 21 as shown in FIG. 5C. If necessary, the completion of this backfilling can be observed by the fibrin glue exiting from the puncture 106. As soon as this occurs, the physician terminates further movement of the syringes 86 and 87 and then while still holding the handle 44 to retain the closure assembly 32 in place, permits the fibrin glue to set up or cure within the puncture 106 for a period of time suitable to permit the fibrin glue to form a sticky adherent clot in the puncture 106 but to prevent the fibrin glue forming a clot which is too firm so as to preclude easy withdrawal of the closure device 21. Typically this ranges from a period of time of 30 seconds to 15 minutes and preferably a period of time of approximately 1-2 minutes. The aforementioned biological sealants only adhere to collagen-containing tissues which prevents them from bonding to the flexible elongate tubular member 22. As soon as the physician determines that the fibrin glue has assumed the desired state, the button 47 carried by the handle 44 is engaged by the finger of the physician's hand and moved out of the slot 52 and then retracted proximally in the slot 49 to cause proximal movement of the push-pull wire 41 to cause a gradual straightening of the closure mechanism 34 to bring it substantially within the interior of the lumen 26 thereby permitting collapse of the flexible membrane 36 so that it can assume a generally sock-like configuration. Thus as soon as the button 47 has been moved to its most proximal position and moved into the notch 51, the closure device 21 can gently be pulled from the seal 116 provided in the puncture 107. The hole (not shown) left in the sealant 116 after withdrawal of the flexible elongate tubular member 22 and the membrane 36 carried thereby closes on itself due to the sufficiently gel-like state of the fibrin glue. Thereafter, the site of the puncture 106 is observed to ascertain whether or not bleeding is occurring therefrom. An excellent biological seal is formed with nothing remaining at the puncture site except for the biological sealant which within a relatively short period of time as for example 1-2 weeks will be absorbed by the body.

From the foregoing it can be seen that there has been provided a closure device and a method for utilizing the same which makes it possible to quickly and efficaciously close the puncture which has been made necessary for performing a desired medical procedure as for example an angioplasty procedure. An excellent seal is formed even though anticoagulants have been introduced into the blood of the patient during the procedure to prevent the formation of clot. The application of fibrin glue in this manner permits the formation of a good clot to seal the puncture without danger of re-bleeding occurring.

It also should be appreciated that during this procedure in performing the closure of the puncture site, blood can continue to flow substantially unimpeded through the lumen 104 of the vessel. This lack of obstruction is made possible because of the small size of the distal extremity of the closure device 21 and also because of the small size of the closure assembly 32 carried by the distal extremity 24 of the device 21. When the closure assembly 32 is deployed as hereinbefore described, it has a relatively small diameter in comparison to the size of the lumen into which it is introduced. In addition it has a flat planar configuration which, when brought into engagement with the inner surface of the wall 103, is substantially flush with the inner surface of the wall 103. Even when the closure assembly 32 is being de-deployed it occupies very little space as it is being withdrawn.

Another embodiment of the closure assembly is shown in FIG. 6 which can be utilized in place of the closure assembly 32 on the distal extremity 24 of the flexible elongate tubular member 22 carried by the handle 44. As shown, the closure assembly 131 consists of a closure mechanism 132 which is covered by a flexible impermeable membrane 133. The closure mechanism 132 can be formed of the same superelastic or shape memory material as the closure mechanism 34 but rather than having a coil-like configuration such as shown in FIG. 1, 3 and 4, it includes a different complex geometrical configuration as for example a flower-like configuration as shown in FIG. 6. Thus it can be formed of a Nitinol ribbon or wire of a single length having ends 137 and 138 which are secured to the distal extremity 43 of the push-pull wire 41 in a manner similar to that hereinbefore described. The wire ribbon 136 has been annealed to have a super-elastic or shape memory form for the flower-like configuration shown in which a plurality of loops 141, as for example three as shown are provided on the wire ribbon 136. The loops 141 are oval shaped, approximately equal in size and have curved outer extremities 142. The loops 141 lie in a single plane and have the longitudinal axes of the loops spaced apart by equal angles of about 120°. It should be appreciated that if desired, additional loops can be provided with the loops being spaced equally over 360°. Since the loops 141 correspond to the shape of petals of a flower, the configuration shown in FIG. 6 can be described as a flower-like arrangement in which the loops 141 lie in a common plane which is generally perpendicular to the longitudinal axis of the flexible elongate member 22.

The membrane 133 which forms a part of the closure assembly 131 can be formed of the same material as the membrane 36 and can be secured in the same manner to the tubular member 22 so that when the closure mechanism 132 is in a retracted position within the lumen 26 it also can be provided with folds in the same manner as the membrane 36. The closure mechanism 132 can be straightened in a similar manner and brought into a retracted position similar to the closure mechanism 34. The closure assembly 131 also can be deployed in a similar manner. When deployed, it will cause the impermeable membrane to assume a generally flat planar configuration which is still substantially in the form of a circle as determined by the outer curved extremities 142 of the loops 141 with very slight variations from a circle between the outer extremities of adjacent loops. Thus a good seal can be formed with the wall 103 of the vessel 107 in the same manner as with the closure assembly 32. Thus it can be seen that the operation and use of the closure assembly of FIG. 6 can be very similar to that described for use of the closure assembly 32 and with generally the same attendant advantages. It should be appreciated that other arrangements of closure mechanisms can be provided for causing appropriate deployment of the impervious membrane to form a seal without departing from the scope of the present invention. The sizes and shapes of the closure assemblies can be selected to be appropriate for the puncture to be occluded. Thus for example the flower arrangement shown in FIG. 6 can have the same size as the coil arrangement shown in FIGS. 1, 3 and 4 or alternatively can be decreased or increased in size as desired. Furthermore, by altering the number of petals or loops, the shape can also be varied from that of a circle to that of substantially a triangle or square.

Another embodiment of a closure device incorporating the present invention is shown in FIG. 7–10. The closure device 151 is shown therein. The closure device is very similar to that shown in FIG. 1 with the principal difference being in the type of closure assembly utilized on the distal extremity 24 of the flexible elongate tubular member 22. Thus all of the parts of the closure device 151 carry the same numbers as the closure device 21 shown in FIG. 1 to the distal extremity 24 on which the closure assembly 156 is carried. The closure assembly 156 consists of a closure mechanism 157 which is covered by a flexible impermeable membrane 158. The closure mechanism 157 consists of a plurality of rod-like elements 161, struts or arms of at least three in number which are circumferentially spaced apart and have proximal ends 162 which are embedded in the distal extremity 24 of the flexible elongate tubular member 22. This can be accomplished in a suitable manner such as by extruding the plastic forming the tubular member over the proximal ends 162 or alternatively by placing axially aligned bores in the distal extremity 24 and securing the proximal ends 162 therein by suitable means such as an adhesive. The exposed portions of the rod-like elements 161 as shown in FIG. 7 are formed of a suitable material such as stainless steel or Nitinol and are inclined inwardly in a distal direction to provide a truncated cone-like shape. The distal ends 163 of the rod-like elements 161 can be bonded or fastened together in a suitable manner such as by welding or solder to provide a generally hemispherical tip 166 which is also secured to the distal extremity 43 of the push-pull wire 41. The rod-like elements 161 are provided with weakened regions or notches or memorized bending points 171 approximately a substantially equal distance from the proximal and distal ends 162 and 163 to form hinge points 171. The lengths of the exposed portions of the rod-like elements 161 may be selected to correspond to a selected diameter of the closure mechanism 157.

The membrane 158 which covers the closure mechanism 157 has a sock-like configuration with a closed end 176 which overlies the hemispherical tip 166 and an a open end which is defined by the circular rim 177 which is bonded to the exterior surface of the distal extremity 24 of the flexible elongate tubular member 22 by an adhesive (not shown).

Operation and use of the closure device 151 may now be briefly described as follows. It should be appreciated that imposition of the button 47 with respect to the notches 51 and 52 is reversed in that the button is positioned in the notch 52 when the closure assembly 156 is in the de-deployed or unexpanded condition as shown in FIG. 7 rather than in the notch 51. A closure device 151 can be introduced into the sheath 111 in the unexpanded condition shown in FIG. 7 in the manner hereinbefore described with respect to the device 21 and after the closure assembly 156 is within the lumen 104 of the vessel 107 the closure assembly 156 can be deployed or moved to an expanded position by moving the button 47 proximally to cause a pulling force to be applied to the hemispherical tip 166 to cause a pushing force to be applied to the rod-like elements 161 to cause them to be bowed outwardly and to bend or fold about the hinge points 171 and at the same time to carry with them the membrane 158. Continued movement of the button 47 proximally until it reaches the slot 51 will cause the rod-like elements 161 to cause the portions 161a to generally overlie the portions 161b and to extend radially from the longitudinal axis of the flexible elongate tubular member 22 at substantially right angles thereto as shown in FIG. 10. The membrane 158 covering the same is similarly caused to assume a generally circular disk-like configuration lying in a single plane which can be brought against the inner surface of the wall 103 of the vessel 107 in the same manner that the closure assembly 32 hereinbefore described is brought into contact with the wall. Thereafter the procedure hereinbefore described can be used for forming the seal with the puncture 106 and to permit introduction of the biological sealant. After this procedure has been completed, the closure mechanism 157 can be de-deployed by moving the same to an unexpanded condition by moving the knob 47 proximally to cause the push-pull wire 41 to move the hemispherical tip 166 distally and to carry with it the membrane 158 until the closure assembly 156 assumes its original unexpanded or de-deployed generally cylindrical configuration which is in alignment with the longitudinal axis of the flexible elongate tubular member 22 as shown in FIG. 7 after which the closure device 151 can be removed to form the desired occlusion for the puncture 106. It should be appreciated that by varying the number of rod-like elements the shape of this closure assembly can similarly be varied so that it may be deployed into planar triangular, square or oval configurations as well. This closure assembly 156 also differs from the closure assembly 32 and the closure assembly 131 in that it can be formed without the use of super-elastic or shape memory material.

Another embodiment of a closure device incorporating the present invention is shown in FIGS. 11, 12 and 13 in which a closure device 191 is shown which is very similar to the closure device shown in FIG. 7 with the exception that the closure assembly carried by the distal extremity 24 of the flexible elongate tubular member 22 is of a different construction from the closure assembly 156. The closure assembly 196 differs from the closure assembly 156 in that the distal extremity 24 of the flexible elongate tubular member 22 carries an additional segment 192 of flexible elongate tubular material which has been bonded or annealed to the tip 31 of the distal extremity 24 of the flexible elongate tubular member 22 and which forms a part of a closure mechanism 197 which is covered by an impermeable flexible membrane 198. The additional segment 192 is constructed of a segment of flexible elongate tubular member which is extruded with only a main circular in cross-section first lumen and without an additional lumen. The second lumen 27 in this device 191 is blocked by the bonded or annealed additional segment 192 and thus no plug is required. To form the closure mechanism 197, the additional segment 192 of the flexible elongate tubular member 22 is provided with a plurality of circumferentially spaced apart longitudinally extending slits 201 of a suitable number to provide a plurality of arcuate segments as for example the four segments 24a, 24b, 24c and 24d as shown in FIGS. 11 and 12. As hereinafter described since the segments 24a, b, c and d are formed of a flexible material, they can be bowed outwardly. The closure assembly 196 also includes a plurality of rod-like elements 202 similar to the rod-like elements 161 and formed of a suitable material such as stainless steel or Nitinol but because of the use of the arcuate segments 24a, b, c and d the rod-like elements 202 need only be approximately one-half the length of the rod-like elements 161. The rod-like elements 202 like the rod-like elements 161 can have a suitable diameter as for example 0.002" to 0.005" (0.05 to 0.127 millimeters) or preferably 0.002" to 0.003" (0.05 to 0.076 millimeters). The rod-like elements 202 are provided with proximal and distal ends 203 and 204. The proximal ends are embedded in the arcuate segments 24a, b, c and d in a suitable manner. For example, the plastic forming the segments can be extruded over the ends 203 or, alternatively, the segments can be provided with bores for receiving the ends 203 which are secured therein by suitable means such as an adhesive (not shown). The rod-like elements 202 extend distally and inwardly to form a truncated cone and have their distal ends 204 interconnected by a generally hemispherical tip 206 formed of solder or a weld which is also bonded to the distal extremity 43 of the push-pull wire 41 as shown in FIG. 11. The rod-like elements 202 are provided with notches or weakened regions or memorized bending points to form hinge points 208 which are preferably in close proximity to the arcuate segments 24a, b, c and d so that the hinge points are close to the junctures between the ends 203 and the adjoining segments 24a, b, c and d. The length of each of the arcuate segments 24a, b, c and d and each of the rod-like elements 202 is approximately equal and corresponds to the desired size of the closure mechanism 197.

The membrane 198 covers the closure mechanism 197 and has a conformation similar to that of the membrane 158 and is provided with a closed end 211 which overlies the hemispherical tip 206 and an open end circumscribed by a rim 212 which is adhered to the additional portion 192 of flexible elongate tubular material annealed to the tip 31 of the distal extremity 24 of the flexible elongate tubular member 22 just proximal of the slits 201 which form the segments 24a, 24b, 24c and 24d and is secured thereto by a suitable means such as an adhesive (not shown).

Operation and use of the closure device 191 as shown in FIGS. 11 and 12 is very similar to that described for the embodiment of the closure device 151 shown in FIG. 7. The closure device as shown in FIG. 11 has the closure assembly 196 in a de-deployed or un-expanded condition with the button 47 being disposed in the notch 52. In connection with sealing a puncture after the distal extremity 24 of the device 191, and in particular the closure mechanism 197, is disposed within the vessel 107 distal of the puncture 106, the closure assembly 196 can be deployed by moving the button 47 proximally to cause pulling on the pull wire 41 to apply compressive forces to the strut-like rod-like elements 202 to cause outward bowing of the same as well as the segments 24a, 24b, 24c and 24d with sharp bends occurring at the hinge points 208 just distal of the arcuate segments 24a, b, c and d. This outward bowing is continued so that the arcuate segments 24a, b, c and d are bent outwardly with respect to the longitudinal axis of the flexible elongate tubular member 22 and similarly the rod-like strut elements 202 are bowed outwardly with respect to the hemispherical tip 206 while carrying along with them the flexible impermeable membrane 198 until the rod-like elements 202 substantially overlie and are generally parallel with the segments 24a, b, c and d as shown in FIGS. 13 and 14 to form a planar disk-like conformation corresponding generally to the disk-like conformations of the embodiments of the closure devices hereinbefore described. Although the conformation as viewed in FIG. 14 has a generally square configuration it can be readily appreciated that by providing additional segments in the distal extremity 24 and a corresponding number of additional rod-like elements, additional arms can be provided for controlling the movement of the membrane 198 so that the outer margin of the membrane has a more generally circular configuration if that be desired. As heretofore described with other embodiments, the configuration may also be oval, triangular or square depending on the number of elements.

After the closure assembly 196 has been deployed as shown in FIGS. 13 and 14 it can be utilized in the manner hereinbefore described with the previous closure devices for forming a seal with the inner surface of the wall 103 and thereafter introducing a biological sealant. After this has been accomplished, the closure assembly 196 can be contracted and de-deployed by moving the button 47 from the notch 51 and pushing it distally to push the hemispherical tip 206 distally and to cause inward collapsing of the segments 24a, b, c and d and the rod-like strut elements 202 until they have been moved into the original de-deployed or contracted positions as shown in FIG. 11 and with the button 47 in the notch 52. Thereafter, the closure device 191 can be retracted in a manner similar to that hereinbefore described with respect to the previous embodiments.

Another embodiment of a closure device incorporating the present invention is shown in FIGS. 15 and 16. The closure device 221 shown therein is similar to that shown in FIG. 1 with the principal differences being that the device 221 utilizes a closure assembly on the distal extremity 24 of the flexible elongate tubular member 22 and a deployment means that incorporate elements that are similar to both the device shown in FIG. 1 and the device shown in FIGS. 7-10. The closure assembly 222 consists of a closure mechanism 223 and an impervious membrane 224 which covers the closure mechanism 223. The closure mechanism 223 can be formed of the same super-elastic or shape memory material as the closure mechanism 34 but rather than having a coil-like configuration it consists of a plurality of circumferentially spaced apart rod-like elements 226 or arms of at least three in number having proximal and distal ends 227 and 228. Thus each rod-like element 226 can be similarly formed of Nitinol ribbon or wire and is annealed with an approximate 180 degree fold located at the midpoint 229 between the proximal 227 and distal 228 ends so that when in a free state the element 226 tends to fold at the midpoint 229 causing the proximal and distal halves 231 and 232 of the rod-like element 226 to substantially overlie one another in a single plane. Means is provided to secure the proximal end 227 of each rod-like element 226 to the deployment mechanism 230 in a manner hereinafter described. The distal ends 228 of the rod-like elements 226 are fastened together in a suitable manner such as by welding or soldering to provide a generally hemispherical tip 233 which is also secured to the deployment mechanism 230 in a manner hereinafter described. Similar to the closure device 151 shown in FIGS. 7-10, the lengths and number of the rod-like elements 226 may be selected to correspond to a selected diameter and shape of the closure mechanism 223.

The membrane 224 which forms a part of the closure assembly 222 can be formed of the same material as the membrane 36 and can be secured in the same manner to the tubular member 22 so that it is provided with folds and functions in the same manner as the membrane 36.

The deployment mechanism 230 consists of a push-pull wire 234 formed of a suitable material such as stainless steel which is slidably disposed in the first or main lumen 26 and has proximal and distal extremities 236 and 237 similar to the push-pull wire 41 with the principal difference being that during formation the push-pull wire 234 is provided with a central lumen or bore 238 extending from the proximal extremity 236 to the distal extremity 237. The push-pull wire 234 has a suitable outside diameter of approximately 0.020" (0.5 millimeters) and an inside diameter of approximately 0.010" (0.25 millimeters). Means is provided for circumferentially securing the proximal ends 227 of the rod-like elements 226 to the distal extremity 237 of the push-pull wire 234 with the secured proximal ends 227 of the elements 226 being equally spaced apart over 360 degrees and with the vertex of each midpoint 229 fold directed outwardly and consists of similar welds or solder forming joints 239 and 241. The proximal end 236 of the push-pull wire 234 extends out of the proximal extremity 23 of the flexible elongate tubular member 22 and is connected to a handle assembly 242 in a manner similar to the device 21. The deployment mechanism 230 includes a second, smaller pull wire 243 which is slidably mounted or disposed within the central lumen 238 of the larger push-pull wire 234 and is provided with proximal and distal extremities 244 and 246. The pull wire 243 is similarly formed of a suitable material such as stainless steel and has a suitable diameter as for example 0.005" to 0.009" (0.12 to 0.22 millimeters). Means is provided for securing the distal extremity 246 of the pull wire 243 to the hemispheric tip 233 and consists of soldering or welding. The proximal end 244 of the smaller pull wire 243 also extends out of the proximal extremity 23 of the flexible elongate tubular member 22 and is operatively connected to the handle assembly 242 which, in addition to carrying means for causing longitudinal movement of the push-pull wire 234 hereinbefore described and shown in FIG. 1, also carries means for causing movement of the pull wire 243 along the longitudinal axis independent of the movement of the push-pull wire 234 in a manner hereinafter described.

The handle assembly 242 is similar to the handle assembly 44 with the principal difference being that the handle assembly 242 also provides access to the proximal end 244 of the smaller pull wire 243. The protrusion 247 of handle assembly 242 and means of securing the push-pull wire 234 to the same is similar to protrusion 48 but the protrusion 247 is also provided with a lumen 248 extending from the proximal end 249 to the distal end 251 of the protrusion 247 and aligned with the central lumen 238 of the proximal extremity 236 of the push-pull wire 234. A handle lumen 250 is provided which extends proximally from the proximal end of the handle slot 255 and is alignment with both the slot 255 and the proximal end 249 of the lumen 248 in the protrusion 247. The handle lumen 250 is provided with an aperture 252 at the proximal end of the handle 242. The proximal end 244 of the smaller pull wire 243 extends proximally out of the proximal end 236 of the push-pull wire 234 into and through the lumen 248 of the protrusion 247 and through the handle lumen 250 slidably extending proximally out of the handle assembly 242 through the aperture 252. Means for fixing the proximal end 244 of the pull wire 243 in a particular position is provided as for example with a simple releasable clamp or knob 253 that prevents the pull wire 243 from sliding distally.

Operation and use of the closure device 221 may now be briefly described as follows. It should be appreciated that operative positions of the button 254 for operation and use of the closure device 221 are similar to positions for button 47 in the closure device 21 shown in FIG. 1. A closure device 221 can be introduced into the sheath 111 in the un-expanded cylindrical or de-deployed configuration shown in FIG. 15 in the manner hereinbefore described with respect to the device 21. The closure assembly 222 also can be deployed and de-deployed in a similar manner with the principal difference being the additional steps of deploying and de-deploying the pull wire 243 in a manner hereinafter described. After the button 254 is similarly utilized to initiate and maintain deployment of the closure assembly 222 by pushing the closure mechanism 223 out of the distal extremity 24 of the flexible elongate tubular member 22, the rod-like elements 226 and the membrane 224 assume a configuration which is substantially in the form of a disk or a flattened circle, the shape being partially determined by the number of the rod-like elements 226. In order to assure assumption of a substantially flat planar configuration by the closure assembly 222 the small pull wire 243 is then pulled proximally and fixed in position by using the clamp 253, while the push-pull wire 234 is held stationary, to cause a pulling force to be applied to the hemispherical tip 233 to cause a pushing force to be applied to the rod-like elements 226 to cause them to further fold about their midpoints 229 so that the proximal and distal halves 231 and 232 of the elements 226 substantially overlie one another in a single plane at a substantially right angle to the longitudinal axis of the flexible elongate tubular member 22. Thereafter the procedure hereinbefore described can be used for establishing a seal of the puncture 106 and to permit introduction of the biological sealant. After this procedure has been completed, the closure assembly 222 can be de-deployed by releasing the clamp 253, permitting the small pull wire 243 to be pushed distally and then similarly completing the de-deployment sequence as hereinbefore described for closure device 21.

It should be appreciated that additional variations of the pull wire assembly may be utilized as for example means may be provided for mounting the pull wire within the lumen of the push-pull wire so that the position of the pull wire is fixed in relation to the longitudinal axis of the flexible elongate tubular member so that with independent longitudinal movement of the push-pull wire a similar pulling force is simultaneously applied to the hemispherical tip to cause a pushing force to be applied to the rod-like elements as hereinbefore described.

It should also be appreciated that other embodiments may incorporate closure assemblies utilizing arcuate segments similar to those shown in FIGS. 11, 12 and 13, absent rod-like elements wherein the distal tip of the push-pull wire is bonded directly to the tip of the distal extremity of the flexible elongate tubular member so that with proximal traction on the push-pull wire compressive forces applied to the arcuate segments cause outward bowing of the same with bends or folds occurring at the midpoints of the segments. An additional closure assembly may include a closure mechanism constructed of super-elastic or shape memory alloy that is deployed by pushing the closure mechanism distally out of the distal extremity of the flexible tubular member and then causing the super-elastic or shape memory alloy mechanism to be twisted by turning the proximal end of the push-pull wire. In various embodiments the impermeable membrane may also be secured directly to the closure mechanism instead of being secured to the distal extremity of the flexible elongate tubular member. Alternatively the membrane may be configured so to only partially cover the closure mechanism as for example only the proximal side of the deployed closure mechanism.

It is apparent from the foregoing that there has been provided a closure device and method for percutaneous access and occlusion of punctures which medical procedures have required being placed in the human body. By varying the size, shape and the rigidity of the closure assembly it is possible to occlude puncture sites and natural tracts of various sizes and in various locations in the body such as laparoscopic puncture sites, intestinal-cutaneous fistulas, fistulas between the intestines, biliary tract of the stomach and the like. The closure assembly establishes the distal boundary for the puncture so that it enables accurate placement of and prevents inadvertent intravascular injection and embolization of the biological sealant. The closure device of the present invention makes possible the use of biological sealants in which for example fibrin glue is utilized and forms a clot which has greater strength than a natural clot formed by the body. In addition it makes it possible to the bypass the natural coagulation system of the human body even though anticoagulants have been administered to the patient during the prior medical procedure or procedures. Although fibrin glue has been discussed as the principal biological sealant, other sealants may be utilized such as collagen, Avitene™ slurries, Gel Foam™ and cellulose, all of which are non-adherent to the closure device. In addition, it should be appreciated that other means of sealant introduction to the flexible elongate tubular member are available. For example, a multi-component sealant such as fibrin glue may, alternatively, be mixed prior to introduction into the flexible elongate tubular member. The shape of the closure mechanism utilized in the closure device of the present invention that abuts the inner surface of the wall through which the puncture extends enlists the normal pressure of the arterial blood flow to help retain the closure assembly in contact with the wall. The closure assembly is small in size and even when being deployed into the blood vessel permits substantially unobstructed blood flow through the vessel to continue during the closure procedure thus avoiding ischemic and thrombotic complications associated with stasis of blood. The small size similarly prevents the closure assembly from damaging or impinging on the opposite wall of the blood vessel during deployment or de-deployment of the device. Since the closure device and method of the present invention does not require long term intravascular deployment of a foreign body such as collagen, intra-arterial anchors or sutures, nor does it utilize balloon technology with the attendant risks of balloon rupture or tearing, there is a greatly reduced risk of life and limb threatening infections and the introduction of particulates or air emboli into the bloodstream. Since the occlusions which are formed in punctures utilizing the closure device and method of the present invention can be accomplished quickly, this facilitates early ambulation of the patient and helps to avoid traditional complications such as arteriovenous fistulas, pseudo-aneurysms, thrombosis and embolism. Since the device is typically disposed of after one use, the danger of transmitting diseases to the blood stream of the patient is greatly reduced. Medical costs to the patient and to society are also thereby reduced.

Although the closure device and method have been described principally in use with the human body it should be appreciated that the closure device and method also can be utilized with animals in a similar manner.

It is apparent from the foregoing that there has been provided a closure device and method for percutaneous access and occlusion of puncture sites in the human body that have distinct advantages over those heretofore provided.

Percutaneous methods are widespread techniques that offer less invasive, safer and more cost-effective diagnostic and therapeutic access to organs of the human body. In order to fully realize the advantages of percutaneous access however, morbidity associated with access sites must be anticipated and prevented wherever possible. Indeed, advanced therapeutic interventions have led to a greater range of access site complications. A patient who suffers such complications must often undergo a more invasive procedure in order to prevent devastating injury to life or limb. Such procedures incur additional risks and costs. Effective percutaneous occlusion of a percutaneous vascular access site that proves to be otherwise difficult to manage is a major achievement. Without such treatment many of the advantages of percutaneous diagnostic and therapeutic procedures are lost. Satisfactory solutions have heretofore been absent in the prior art. The device and method of the present invention obviate many of the morbid side effects associated with puncture sites hereinbefore described.

What is claimed:

1. A device for percutaneously forming a closure of a puncture in the tissue of the human body comprising a flexible elongate tubular member having proximal and distal extremities and extending along a longitudinal axis, the flexible elongate tubular member having a first lumen extending from the proximal extremity to the distal extremity, a closure assembly carried by the distal extremity of the flexible elongate tubular member, the closure assembly including a closure member movable between contracted and expanded positions, a deformable membrane substantially covering the closure member and secured to the distal extremity of the flexible elongate tubular member, a handle carried by the proximal extremity of the flexible elongate tubular member and adapted to be grasped by the human hand and deployment means carried by the handle and including a push-pull element having proximal and distal extremities, said deployment means extending through the flexible elongate tubular member and being coupled to the closure member for moving the closure member between the contracted position permitting introduction into a puncture and the expanded position permitting substantial occlusion of the puncture, and thereafter to the contracted position permitting removal from the puncture.

2. A closure device as in claim 1 wherein the membrane has a closed end and an open end circumscribed by a rim and means for securing the rim to the distal extremity of the flexible elongate tubular member, said membrane being formed to permit movement of the closure member within the membrane during movement between contracted and expanded positions to cause said membrane when the closure assembly is in an expanded position to assume a generally planar configuration lying in a plane which is generally perpendicular to the longitudinal axis of the flexible elongate tubular member with the membrane being disposed on opposite sides of the closure member and lying in generally parallel planes.

3. A closure device as in claim 1 wherein said membrane has a sock-like conformation in at least one position.

4. A closure device as in claim 1 wherein said closure member in an expanded or deployed position is sufficiently rigid so as to provide a supporting framework for the membrane.

5. A closure device as in claim 1 wherein said closure member is formed of a superelastic alloy material which when free has a substantial portion thereof which assumes a generally planar configuration.

6. A closure device as in claim 1 wherein said closure member is formed of a shape memory alloy material which when free has a substantial portion thereof which assumes a generally planar configuration.

7. A closure device as in claim 1 wherein said closure member when free assumes substantially a complex geometrical configuration.

8. A closure device as in claim 7, wherein said closure member when free assumes substantially a coil-like configuration.

9. A device for percutaneously forming a closure of a puncture site in the human body comprising a flexible elongate tubular member having proximal and distal extremities, a closure member carried by the distal extremity of the flexible elongate tubular member and being movable between contracted and expanded positions, said closure member in a contracted position having a diameter of up to 2.0 mm and in an expanded position having a diameter at least 3 mm, a deformable membrane at least partially covering the closure member and carried by the distal extremity of the flexible elongate tubular member and deployment means carried by the proximal extremity of the flexible elongate tubular member and coupled to the closure member for moving the closure member between the contracted position and the expanded position for substantially occluding the puncture.

10. A device for percutaneously forming a closure of a puncture in the tissue of the human body comprising a flexible elongate tubular member having proximal and distal extremities and extending along a longitudinal axis, the flexible elongate tubular member carrying a first lumen extending from the proximal extremity to the distal extremity, a closure assembly carried by the distal extremity of the flexible elongate tubular member and being movable between contracted and expanded positions, the closure assembly including a closure mechanism, an impermeable membrane at least partially covering the closure mechanism and being carried by the distal extremity of the flexible elongate tubular member, a handle carried by the proximal extremity of the flexible elongate tubular member and adapted to be grasped by the human hand and deployment means carried by the handle and including a push-pull wire having proximal and distal extremities, said deployment means extending through the flexible elongate tubular member and being coupled to the closure mechanism for moving the closure assembly from the contracted position able to be introduced into and through a puncture to the expanded position for substantially occluding the puncture, said closure mechanism when free assuming substantially a flower-like, complex geometrical configuration.

11. A device for percutaneously forming a closure of a puncture in the tissue of the human body comprising a flexible elongate tubular member having proximal and distal extremities and extending along a longitudinal axis, the flexible elongate tubular member carrying a first lumen extending from the proximal extremity to the distal extremity, a closure assembly carried by the distal extremity of the flexible elongate tubular member and being movable between contracted and expanded positions, the closure assembly including a closure mechanism, an impermeable membrane at least partially covering the closure mechanism and being carried by the distal extremity of the flexible elongate tubular member, a handle carried by the proximal extremity of the flexible elongate tubular member and adapted to be grasped by the human hand and deployment means carried by the handle and including a push-pull wire having proximal and distal extremities, said deployment means extending through the flexible elongate tubular member and being coupled to the closure mechanism for moving the closure assembly from the contracted position able to be introduced into and through a puncture to the expanded position for substantially occluding the puncture, said closure mechanism including a plurality of arms which when the closure assembly is in a contracted position lie in a generally cylindrical configuration which is in alignment with the longitudinal axis of the flexible elongate tubular member and in an expanded position extend radially from the longitudinal axis at substantially right angles thereto.

12. A closure device as in claim 11 wherein said closure mechanism comprises at least three radially extending arms.

13. A closure device as in claim 11 wherein said arms have proximal and distal ends with the proximal ends being secured to the distal extremity of the flexible elongate tubular member and means bonding together the distal ends of the arms and the distal end of the push-pull wire.

14. A closure device as in claim 11 wherein said arms are formed with hinge points permitting folding of the same during movement of the closure assembly from a contracted position to an expanded position.

15. A closure device as in claim 14 wherein said hinge points are provided in regions intermediate the proximal and distal ends of the arms and wherein portions of the arms disposed on opposite sides of the hinge points overlap each other when the arms are folded.

16. A closure device as in claim 14 wherein the distal extremity of the flexible elongate tubular member is provided with longitudinally extending circumferentially spaced apart slits to form arcuate segments and wherein said arcuate segments form at least a portion of said radially extending arms.

17. A device for percutaneously forming a closure of a puncture in the tissue of the human body comprising a flexible elongate tubular member having proximal and distal extremities and extending along a longitudinal axis, the flexible elongate tubular member carrying a first lumen extending from the proximal extremity to the distal extremity, a closure assembly carried by the distal extremity of the flexible elongate tubular and being movable between contracted and expanded positions, the closure assembly including a closure mechanism, an impermeable membrane at least partially covering the closure mechanism and being carried by the distal extremity of the flexible elongate tubular member, a handle carried by the proximal extremity of the flexible elongate tubular member and adapted to be grasped by the human hand and deployment means carried by the handle and including a push-pull wire having proximal and distal extremities, said deployment means extending through the flexible elongate tubular member and being coupled to the closure mechanism for moving the closure assembly from the contracted position able to be introduced into and through the puncture to the expanded position for substantially occluding the puncture, said closure mechanism including a plurality of circumferentially spaced apart arms having proximal and distal ends, said push-pull wire having a bore extending therethrough, and further including a pull wire slidably disposed in the bore in the push-pull wire and having proximal and distal extremities, means securing the proximal ends of the arms to the distal extremity of the push-pull wire, means securing the distal ends of the arms to the distal extremity of the pull wire, said deployment means including first means carried by the handle for causing movement of said push-pull wire along the longitudinal axis and second means carried by the handle for causing movement of the pull wire along the longitudinal axis independent of the longitudinal movement of the push-pull wire.

18. A device for percutaneously forming a closure of a puncture in the tissue of the human body comprising a flexible elongate tubular member having proximal and distal extremities and extending along a longitudinal axis, the flexible elongate tubular member carrying a first lumen extending from the proximal extremity to the distal extremity, a closure assembly carried by the distal extremity of the flexible elongate tubular and being movable between contracted and expanded positions, the closure assembly including a closure mechanism, an impermeable membrane at least partially covering the closure mechanism and being carried by the distal extremity of the flexible elongate tubular member, a handle carried by the proximal extremity of the flexible elongate tubular member and adapted to be grasped by the human hand, deployment means carried by the handle and including a push-pull wire having proximal and distal extremities, said deployment means extending through the flexible elongate tubular member and being coupled to the closure mechanism for moving the closure assembly from the contracted position able to be introduced into and through a puncture to the expanded position for substantially occluding the puncture and means carried by said flexible elongate tubular member for introducing a biological sealant into the puncture proximal to said closure mechanism, said means including a second lumen extending from the proximal extremity to the distal extremity of said flexible elongate tubular member, said second lumen terminating in an external port positioned adjacent said closure mechanism.

19. A closure device as in claim 18 wherein said means for introducing a biological sealant includes a wye adapter and first and second syringes carried by the wye adapter for carrying and introducing two separate components of a biological sealant into the second lumen.

20. A closure device as in claim 18 wherein said biological sealant is selected from a group consisting of:
(a) fibrin glue; (b) collagen; (c) Avitene; (d) cellulose; (e) gelatin; (f) Gelfoam.

21. A device for percutaneously forming a closure of a puncture in the tissue of the human body comprising a flexible elongate tubular member having proximal and distal extremities and extending along a longitudinal axis, the flexible elongate tubular member carrying a first lumen extending from the proximal extremity to the distal extremity, a closure assembly carried by the distal extremity of the flexible elongate tubular member and being movable between contracted and expanded positions, the closure assembly including a closure mechanism, an impermeable membrane at least partially covering the closure mechanism and being carried by the distal extremity of the flexible elongate tubular member, a handle carried by the proximal extremity of the flexible elongate tubular member and adapted to be grasped by the human hand and deployment means carried by the handle and including a push-pull wire having proximal and distal extremities, said deployment means extending through the flexible elongate tubular member and being coupled to the closure member for moving the closure assembly from the contracted position able to be introduced into and through a puncture to the expanded position for substantially occluding the puncture, said closure assembly in a de-deployed configuration having a diameter ranging from 1.0 mm to 2.0 mm and said closure assembly in a deployed configuration having a diameter ranging from 3 to 7 mm, said closure assembly in a deployed configuration having a thickness of approximately 0.05 to 1 mm.

22. A method for percutaneously forming a closure of a puncture in tissue in the human body, the puncture having proximal and distal ends, by use of a closure device having a flexible elongate tubular member having proximal and distal extremities and a longitudinal axis and a first lumen extending from the proximal extremity to the distal extremity, a closure assembly carried by the distal extremity of the flexible elongate tubular member movable between contracted and expanded positions, said closure assembly including a closure mechanism and a flexible impermeable membrane covering the closure mechanism and being carried by the distal extremity of the flexible elongate tubular member, a handle carried by the proximal extremity of the flexible elongate member and deployment means carried by the handle and including a push-pull wire extending through the first lumen of the flexible elongate member and coupled to the closure mechanism for moving the closure assembly between expanded and contracted positions and in an expanded position providing a closure assembly which lies substantially in a plane generally perpendicular to the longitudinal axis of the flexible elongate member, the method comprising introducing the distal extremity of the flexible elongate tubular member and the closure assembly carried thereby through the puncture so that the closure assembly is disposed distally of the puncture, moving the closure assembly from a contracted position to an expanded position so that it lies substantially in a plane and pulling the flexible elongate tubular member proximally to bring the closure assembly into contact with the distal end of the puncture to seal the puncture and introducing a biological sealant to cause the biological sealant to surround the distal extremity of the flexible elongate member and to fill the puncture, permitting the biological sealant to cure for a predetermined amount of time, thereafter moving the closure assembly from the expanded position to a contracted position and removing the closure device from the biological sealant and permitting the biological sealant to close off any remaining hole to form closure of the puncture.

23. A method as in claim 22 together with the step of waiting a period of time ranging from one to fifteen minutes and then moving the closure assembly from the expanded position to the contracted position.

24. A method as in claim 23 wherein tissue in the human body includes a vessel having a wall with a blood carrying lumen therein and in which the puncture extends through the wall of the vessel and wherein the closure assembly is introduced into the lumen through the puncture and is moved from a contracted to an expanded position within the lumen and is brought into engagement with the wall of the vessel to form a seal between the wall of the vessel and the puncture.

25. A device for expansion within a blood vessel defined by a wall having a puncture therein comprising an elongate tubular member having proximal and distal extremities and having a longitudinal axis, the distal extremity being sized so that it is adapted to extend through the puncture in the wall, an expansion assembly carried by the distal extremity and movable between contracted and expanded positions, the expansion assembly including an expansile member movable between contracted and expanded positions and a deformable membrane covering the expansile member, said deformable membrane being sized so as to be capable of expanding as the expansile member moves from the contracted position to the expanded position and overlying and underlying the expansile member and deployment means carried by the proximal extremity of the elongate tubular member and adapted to be operated by the human hand for controlling movement of the expansile member between the contracted and expanded positions.

26. A device as in claim 25 wherein said expansile member is comprised essentially of a superelastic material.

27. A device as in claim 26 wherein said expansile member has a configuration in the free state that is substantially a coil shape.

28. A device as in claim 25 wherein said membrane is secured to distal extremity of the elongate tubular member.

29. A device as in claim 25 wherein said membrane is free to stretch relative to the expansile member.

30. A device as in claim 25 wherein said membrane has a closed end and an open end circumscribed by a rim, said membrane being disposed on opposite sides of the expansile member in the expanded position.

31. A device as in claim 25 wherein said membrane prior to expansion has a sock-like conformation.

32. A device as in claim 25 wherein said elongate tubular member is flexible.

33. A device as in claim 25 wherein said elongate tubular member has a lumen extending from the proximal to the distal extremity.

34. A device as in claim 30 wherein said closed end is free to move relative to said rim.

35. A percutaneous closure device for sealing a puncture in a wall defining a blood vessel having a lumen through which blood flows comprising an elongate tubular member having proximal and distal extremities and a longitudinal axis, an expansile assembly carried by the distal extremity of the tubular member, said expansile assembly including an expansile member and an expansile membrane extending over the expansile member, said expansile assembly being movable between contracted and expanded positions, said expanded assembly when in the contracted position being sized so that it is adapted to be moved through the puncture and into the lumen, and operator means carried by the tubular member accessible from the proximal extremity of the tubular member for causing movement of the expansile assembly from the contracted to the expanded position after the expansile assembly has been introduced into the lumen of the blood vessel to engage the wall of the vessel to form a closure for the puncture.

36. A device as in claim 35 wherein said expansile member is formed of a superelastic material having a shape memory at body temperature corresponding generally to the expanded position.

37. A device as in claim 36 wherein the expansile membrane in the expanded position of the expansile assembly lies in a plane.

38. A device as in claim 37 wherein the expansile membrane overlies and underlies the plane of the expansile member when the expansile assembly is in the expanded position.

39. A device as in claim 37 wherein the expansile membrane is sized so that it is made taut by the expansile member when the expansile assembly is in the expanded position.

40. A device as in claim 39 wherein the expansile membrane in the contracted position is in the form of a sock having an open end secured to the distal extremity of the elongate tubular member and enclosing the expansile member.

41. A method for percutaneously forming a closure of a puncture in tissue in the human body, the puncture having proximal and distal ends, by use of a closure device having a elongate tubular member having proximal and distal extremities and a longitudinal, a closure assembly carried by the distal extremity of the elongate tubular member movable between contracted and expanded positions, said closure assembly including a closure mechanism and a deformable membrane covering the closure mechanism and carried by the distal extremity of the elongate tubular member and deployment means carried by the proximal extremity of the elongate tubular member and adapted to be operated by the human hand, said deployment means being coupled to the closure assembly for moving the closure assembly between expanded and contracted positions, the method comprising introducing the distal extremity of the elongate tubular member and the closure assembly carried thereby through the puncture so that the closure assembly is disposed distally of the puncture, moving the closure assembly from a contracted position to an expanded position so that it lies substantially in a plane and pulling the elongate tubular member proximally to bring the closure assembly into contact with the distal end of the puncture to seal the puncture and, after a predetermined period of time, moving the closure assembly from the expanded position to a contracted position and removing the closure device from the remaining hole to form closure of the puncture.

42. A method for expanding a device within a blood vessel having a lumen defined by a wall having a puncture therein by use of a device comprising an elongate tubular member having proximal and distal extremities and having a longitudinal axis, the distal extremity being sized so that it is adapted to extend through the puncture in the wall, an expansion assembly carried by the distal extremity and movable between contracted and expanded positions, the expansion assembly including an expansile member movable between contracted and expanded positions and a deformable membrane covering the expansile member, said deformable membrane being sized so as to be capable of expanding as the expansile member moves from the contracted position to the expanded position and overlying and underlying the expansile member and deployment means carried by the proximal extremity of the elongate tubular member and adapted to be operated by the human hand for controlling movement of the expansile member between the contracted and expanded positions, the method comprising introducing the distal extremity of the elongate tubular member and the expansion assembly carried thereby through the puncture so that the expansion assembly is disposed distally of the puncture, moving the expansion assembly from a contracted position to an expanded position and pulling the elongate tubular member proximally to bring the expansion assembly into contact with the wall of the blood vessel to seal the puncture and, after a predetermined period of time, moving the expansion assembly from the expanded position to a contracted position and removing the expansion device from the remaining hole to form closure of the puncture.

* * * * *